(12) United States Patent
Garcia et al.

(10) Patent No.: US 8,540,540 B2
(45) Date of Patent: Sep. 24, 2013

(54) LUMINOUS ENVY TANNING FLOAT SYSTEM

(76) Inventors: Cheri Chafin Garcia, Frisco, TX (US); Robert Garcia, Frisco, TX (US)

(*) Notice: Subject to any disclaimer, the term of this patent is extended or adjusted under 35 U.S.C. 154(b) by 121 days.

(21) Appl. No.: 13/078,617

(22) Filed: Apr. 1, 2011

(65) Prior Publication Data
US 2012/0252292 A1  Oct. 4, 2012

(51) Int. Cl.
*B63C 9/08* (2006.01)

(52) U.S. Cl.
USPC .......................................................... 441/129

(58) Field of Classification Search
USPC .................................................. 441/129–131
See application file for complete search history.

(56) References Cited

U.S. PATENT DOCUMENTS

| | | | | |
|---|---|---|---|---|
| 4,876,756 | A * | 10/1989 | Vaccaro | 5/710 |
| 4,905,332 | A | 3/1990 | Wang | |
| 4,964,183 | A * | 10/1990 | LaForce, Jr. | 5/421 |
| 4,986,781 | A | 1/1991 | Smith | |
| 5,101,823 | A * | 4/1992 | Smith | 607/81 |
| 5,186,667 | A | 2/1993 | Wang | |
| 5,879,377 | A * | 3/1999 | Mullins | 607/95 |
| 6,527,343 | B2 | 3/2003 | Scheurer et al. | |
| 2007/0013222 | A1* | 1/2007 | Benfield | 297/452.14 |
| 2009/0078249 | A1* | 3/2009 | Liu | 126/684 |

* cited by examiner

*Primary Examiner* — Stephen Avila
(74) *Attorney, Agent, or Firm* — Thrasher Associates

(57) ABSTRACT

Luminous Envy Tanning Float is a device to promote even and accelerated tanning adapted for use in water preferably comprises the following components: a pair of angled, reflective, tan; a cushioned core-supported portion; a pillow; at least one cup holder; and at least one warning label to prevent sun-burning. A user-sunbather is comfortably supported via the inflatable flotation device for even and accelerated tanning during at least one sunbathing period on a body of water and/or land.

2 Claims, 6 Drawing Sheets

LUMINOUS ENVY TANNING FLOAT SYSTEM

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

BACKGROUND OF THE INVENTION

1. Field of the Invention

The present invention relates generally to the field of floatation devices and more specifically relates to an inflatable flotation device to promote even and accelerated tanning adapted for use in water and/or land.

2. Description of the Related Art

Sun tanning is the act of exposing the skin to ultraviolet (UV) radiation, for the purpose of darkening skin color, either during sun bathing or using artificial sources, such as tanning beds. Tanning is a natural process in which the skin creates the brown-colored pigment called melanin, to protect it against the overexposure UV rays in sunlight. It can also be caused by artificial UV radiation. The ultraviolet frequencies responsible for tanning are often divided into the UVA and UVB ranges. Many individuals in modern society enjoy sun tanning outdoors on a body of water.

An air mattress is an inflatable mattress/sleeping pad. Due to its buoyancy, it is also often used as a water toy/flotation device. The air mattress may used to recline on the water surface. Conventional tanning floats such as air mattresses are often not as effective as consumers would like them to be. These air mattresses tend to employ inefficient, skinny-profile designs that make it difficult to roll over or change positions as well as not reflecting sunrays back onto the user Tanning floats also do not usually have a face rest making it uncomfortable for users to lie on their stomach to sun their backs. Therefore a need exists for a tanning float that shortens the amount of time it takes for a user-sunbather to comfortably achieve an even tan.

Various attempts have been made to solve the above-mentioned problems such as those found in U.S. Pat. Nos. 4,964,183; 5,186,667; 5,101,823; 4,986,781; 4,905,332; and 6,527,343. This prior art is representative of support structures to promote tanning. None of the above inventions and patents, taken either singly or in combination, is seen to describe the invention as claimed.

Ideally, an inflatable flotation device to promote even and accelerated tanning adapted for use in water should be convenient and user-friendly and yet, would operate reliably and be manufactured at a modest expense. Thus, a need exists for a Luminous Envy Tanning Float system that is designed to provide a user-sunbather with an inflatable tanning device designed for comfortable fast and even tanning during outdoor sunbathing episodes.

BRIEF SUMMARY OF THE INVENTION

In view of the foregoing disadvantages inherent in the known inflatable flotation device art, the present invention provides a novel Luminous Envy Tanning Float. The general purpose of the present invention, which will be described subsequently in greater detail is to promote an even and comfortable tanning means. Luminous Envy Tanning Float provides consumers with an inflatable tanning device designed for fast and even tanning. This unique item is made with highly reflective materials and includes side panels that direct the sunrays onto the user from various angles.

The present inflatable flotation device to promote even and accelerated tanning adapted for use in water as described herein preferably comprises the following components: a pair of angled, reflective tan wings; a cushioned core-supported portion; a pillow; at least one cup holder; and at least one warning label to prevent at least one sunburn. A user-sunbather is comfortably supported via the inflatable flotation device for even and accelerated tanning during at least one sunbathing period on a body of water (or alternately on land.)

The inflatable flotation device measures approximately three-feet in width, six-feet wide, and eight-inches thick when in an in-use condition wherein the inflatable flotation device is inflated with air. Further, the three-foot width provides the user-sunbather room to find a position that exposes a body of the user-sunbather to the sun without tipping over into the water. Further, the inflatable flotation device reflects sunrays onto the user-sunbather. The device may also comprise side air chambers that angle out 45 degrees from a main body of the inflatable flotation device. The inflatable flotation device may comprise a user-preferred color.

The pair of angled reflective, tan wings to direct the sunrays onto a user-sunbather from various angles may comprise polyethylene terephthalate (boPET) (or suitable equivalent) to increase exposure to sunlight during sunbathing period(s). Further, the pair of pair of angled, reflective, tan wings may be permanently attached to aid cushioned core-supported portion providing supports for arms of the user-sunbather to be positioned for tanning. Additionally the pair of angled, reflective, tan wings may be angled at approximately a 45-degree angle relative to the cushioned core-supported portion.

The cushioned core-supported portion preferably comprises polyethylene terephthalate (boPET) to increase exposure to sunlight during at least one sunbathing period. The cushioned core-supported portion comprises a cushioning surface for a core-support of the user-sunbather. In preferred embodiments the pillow is removeably-attachable to the cushioned core-supported portion and is inflatable to a user-preferred volume. The pillow provides a neck angling at a 45-degree angle to a final thickness of approximately eight-inches at the top of the head. The pillow is contoured to fit a face of the user-sunbather when in a face-down position while lying on the inflatable flotation device. The cup holder (optional) is on a far right side of the inflatable flotation device approximately 28-inches from a bottom position of said pillow.

A kit is embodied herein for the Luminous Envy Tanning Float system comprising: the inflatable flotation device; the removably-coupleable pillow; a matching cup; and a set of user instructions.

In accordance with the embodiments of the present invention a preferred method of use is disclosed herein comprising: step one inserting the inflatable flotation device into a body of water; step two laying on the inflatable flotation device; step three sun-bathing while supported by inflatable flotation device and thereby promoting an even and accelerated tan; and step four a user removing themselves from inflatable flotation device when finished sun-bathing.

The present invention holds significant improvements and serves as a Luminous Envy Tanning Float system. For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, Luminous Envy Tanning Float system device constructed and operative according to the teachings of the present invention.

The various embodiments of the present invention will hereinafter be described in conjunction with the appended drawings, wherein like designations denote like elements.

DETAILED DESCRIPTION

As discussed above, embodiments of the present invention relate to floatation devices and more specifically relates to an inflatable flotation device to promote even and accelerated tanning adapted for use in water.

Figure 1:
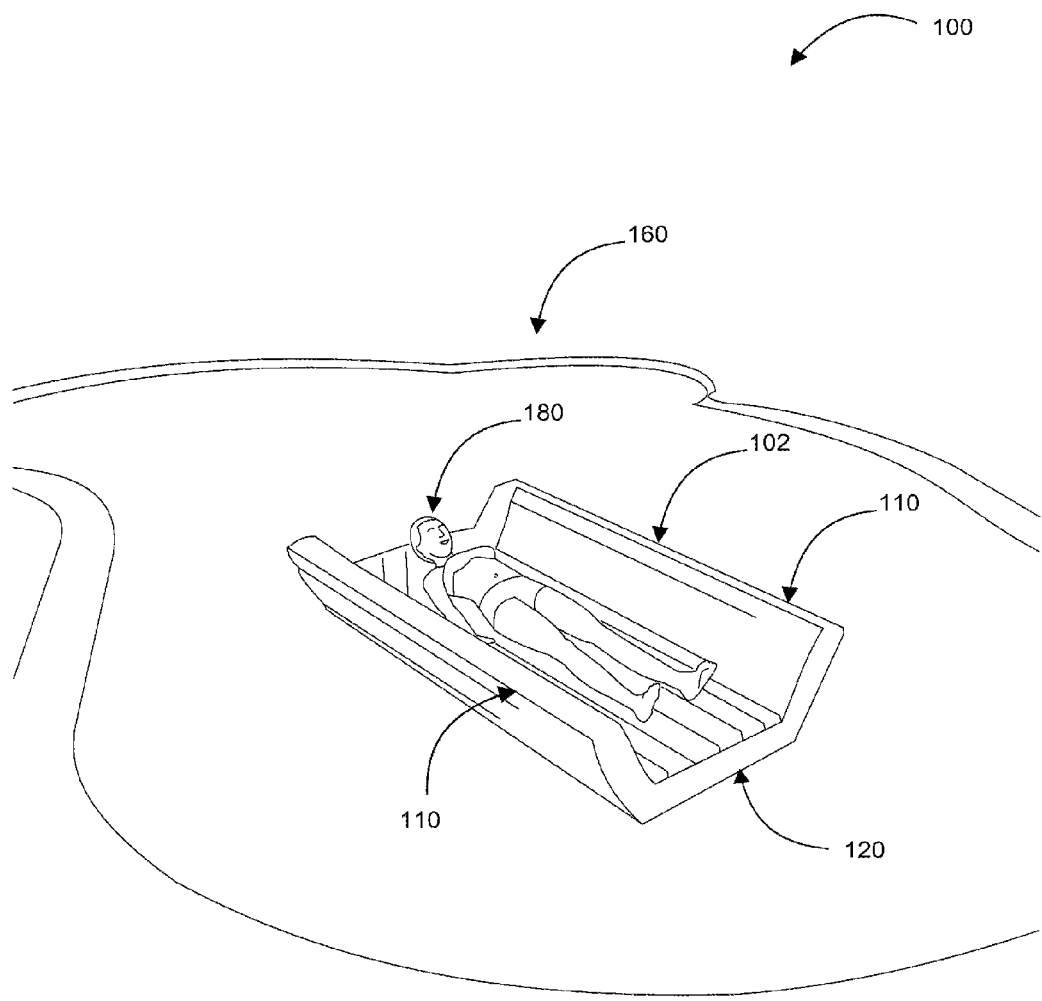
FIG. 1 shows a perspective view illustrating a Luminous Envy Tanning Float system in a face-up 'in-use' condition according to an embodiment of the present invention.
Figure 2:
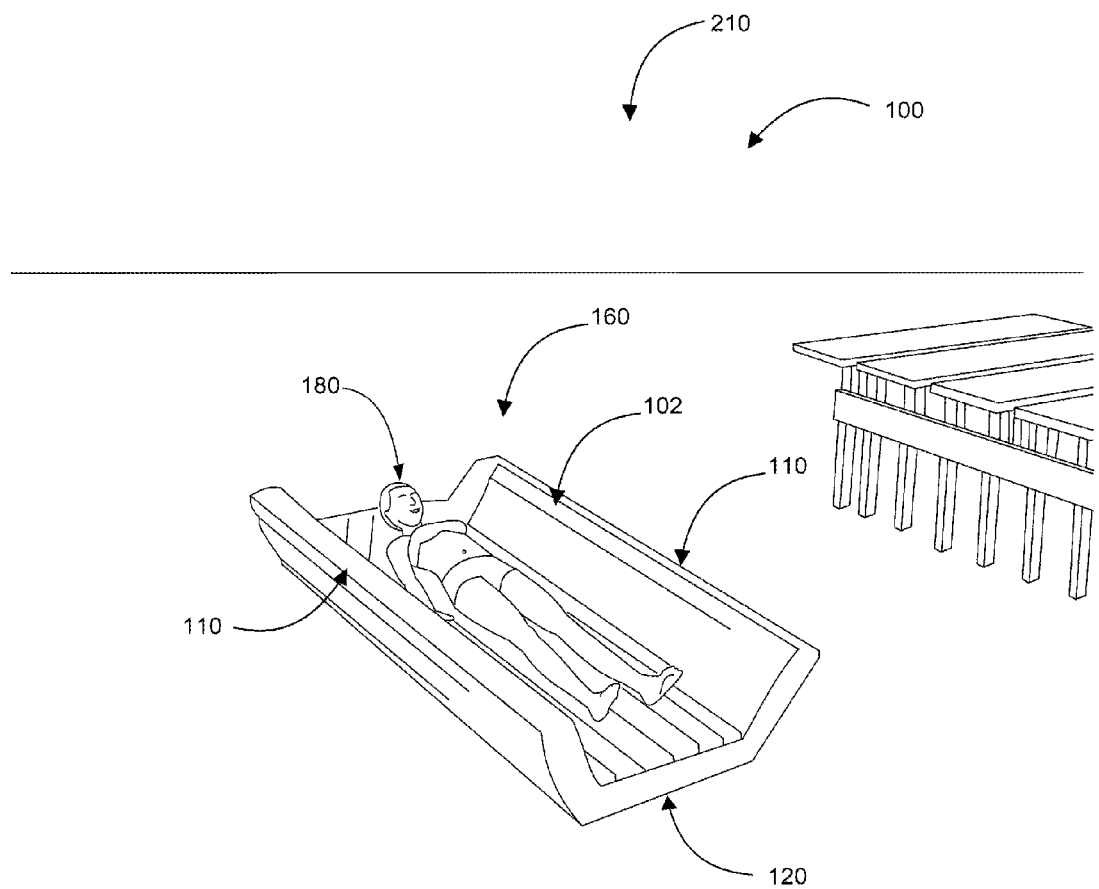
FIG. 2 is a perspective view illustrating an inflatable flotation device of the Luminous Envy Tanning Float on land according to an embodiment of the present invention.
Figure 3:
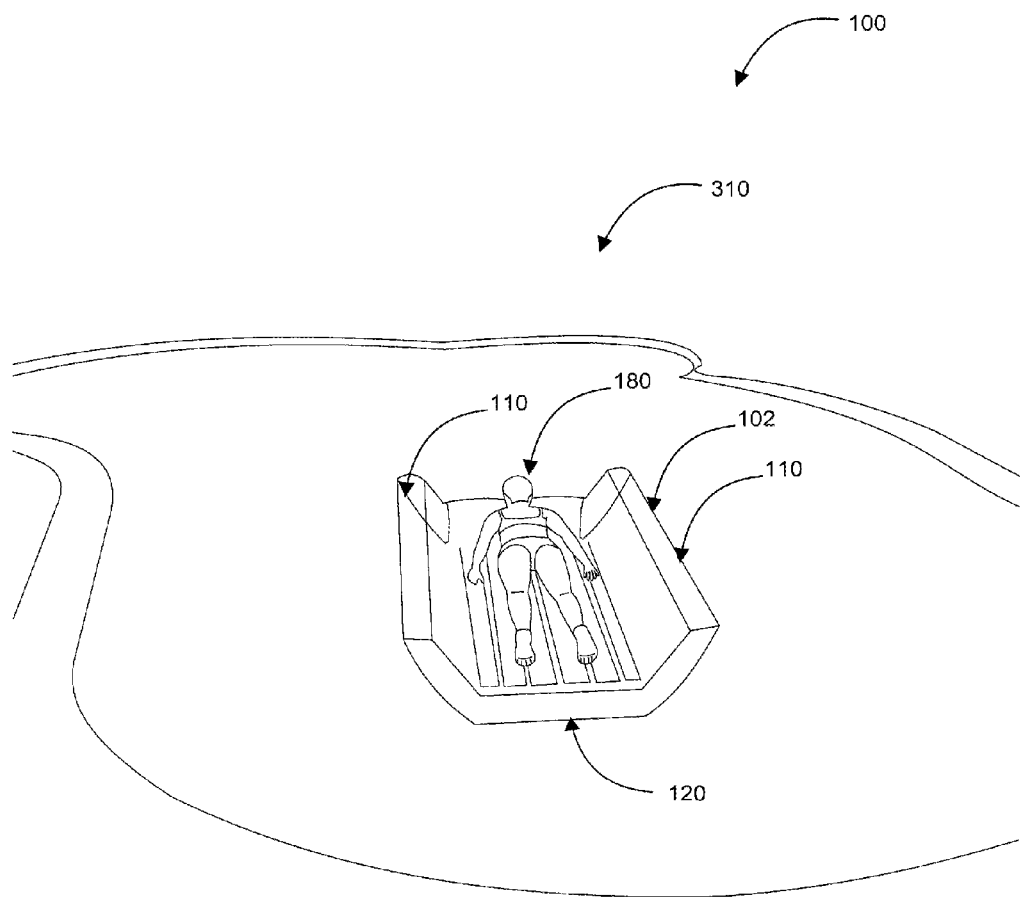
FIG. 3 is a perspective view illustrating the Luminous Envy Tanning Float system in a face-down 'in-use' condition according to an embodiment of the present invention of FIG. 1.

Referring now to FIG. 1-3 showing perspective views of Luminous Envy Tanning Float system 100 in in-use conditions according to an embodiment of the present invention. Luminous Envy Tanning Float system 100 comprises inflatable flotation device 102. Inflatable flotation device 102 as shown preferably promotes even and comfortable tanning means. Further, user-sunbather 180 is comfortably supported via inflatable flotation device 102 for even-tanning during at least one sunbathing period (on water or land.)

Inflatable flotation device 102 preferably comprises a pair of angled, reflective tan wings 110; cushioned core-supported portion 120; and pillow 130. Inflatable flotation device 102 preferably measures approximately three-feet in width, six-feet in length, and eight-inches thick when in an in-use condition (as illustrating in in-use condition 106, 'in-use' condition 210, and 'in-use condition 310) wherein inflatable flotation device 102 is inflated with air or other suitable medium. Other sizes may be used in various embodiments. The three-foot width of inflatable flotation device 102 may provide user-sunbather 180 room to find a position that exposes user-sunbather 180 to the sun without tipping over into the water, thereby increasing stability and sunray garnering means. Inflatable flotation device 102 preferably comprises clear plastic, however other translucent materials may be used. Additionally, inflatable flotation device 102 may comprise a user-preferred color such as red, orange, yellow, green, blue, violet, or pink. Other colors may be selected according to user-preference.

Preferably pair of angled, reflective, tan wings 110 are permanently attached to cushioned core-supported portion 120 providing supports for arms of user-sunbather 180 to be positioned for tanning. User-sunbather 180 may comfortably be supported via inflatable flotation device 102 for even and accelerated tanning during at least one sunbathing period on a body of water as shown in FIGS. 1 & 3. Pair of angled, reflective, tan wings 110 preferably directs the sunrays onto user-sunbather 180 from various angles, thereby creating an even tan.

Cushioned core-supported portion 130 preferably comprises a cushioning surface for a core support of user-sunbather 180. The core support may be a back support as shown in FIGS. 1 & 2 or a front support as shown in FIG. 3. Further, cushioned core-supported portion 130 preferably comprises foam, however other suitably deformable materials may be used such as polypropylene, polyurethane, honeycomb or the like. Cushioned core-supported portion 130 preferably is the horizontally position of inflatable flotation device 102 where user-sunbather 180 lays when sunbathing in a substantially planar position.

It should be noted that inflatable flotation device 102 may be used during non-sunbathing periods such as in the evening when there are no Ultra-Violet rays radiating from the sun. Further, inflatable flotation device 102 does not need to be used on a body of water and may be used on a hard, non-fluid surface such as a backyard of user-sunbather 180 as shown in 'in-use' condition 210.

Pillow 130 may be removeably-attachable to cushioned core-supported portion 120. Pillow 130 is also preferably inflatable to a user-preferred volume and contoured to fit a face of user-sunbather thereby permitting user-sunbather 180 to lay in a face down position while laying upon inflatable flotation device 102. This face-down position is shown in 'in-use condition 310. Pillow 130 may or may not comprise a hole. Dotted lines may also be used in the figures to indicated optional features. Pillow 130 may also be removeably-attachable to cushioned core-supported portion 120 and may provide a neck angling at a 45-degree angle to a final thickness of approximately eight-inches at the top of the head.

Figure 4:
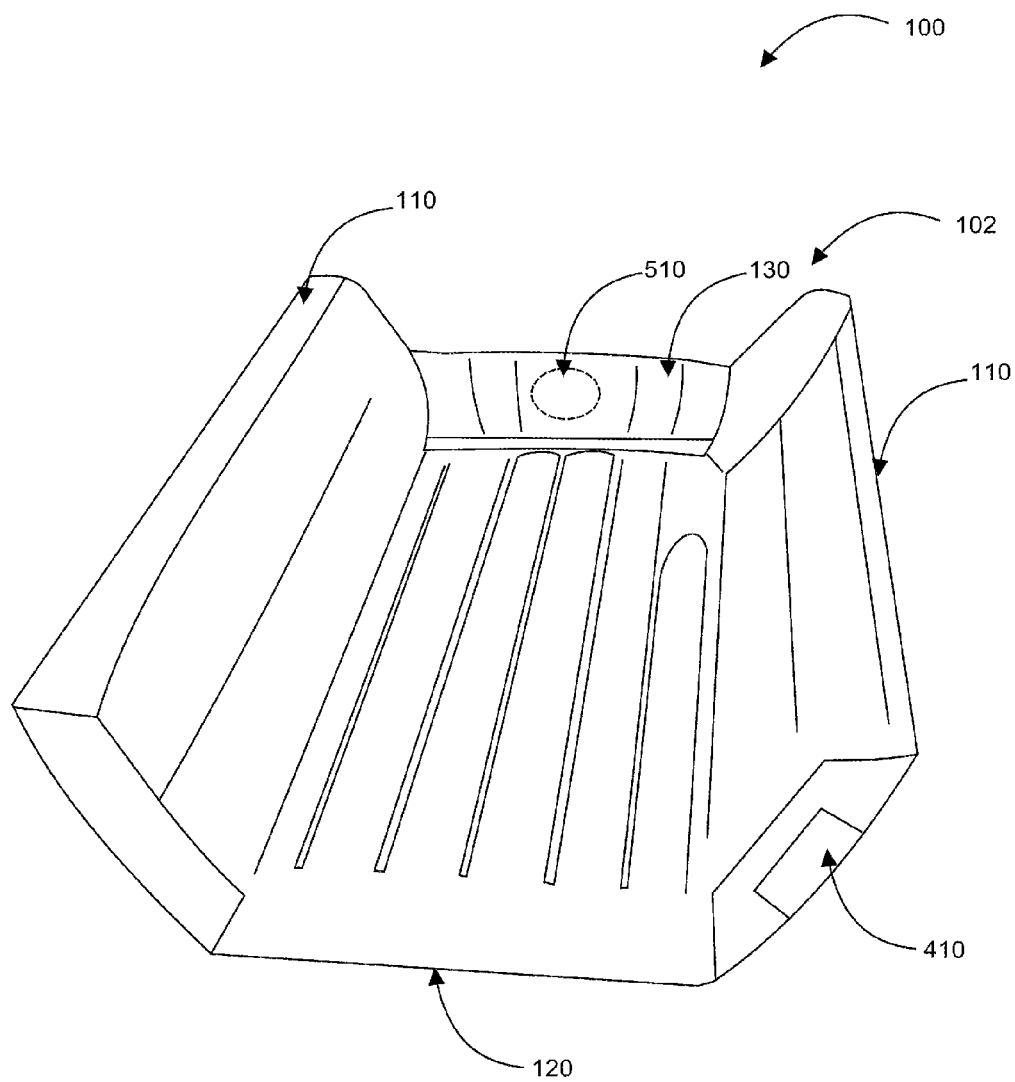
FIG. 4 shows a perspective view illustrating another view of the inflatable flotation device of the Luminous Envy Tanning Float system according to an embodiment of the present invention.
Figure 5:
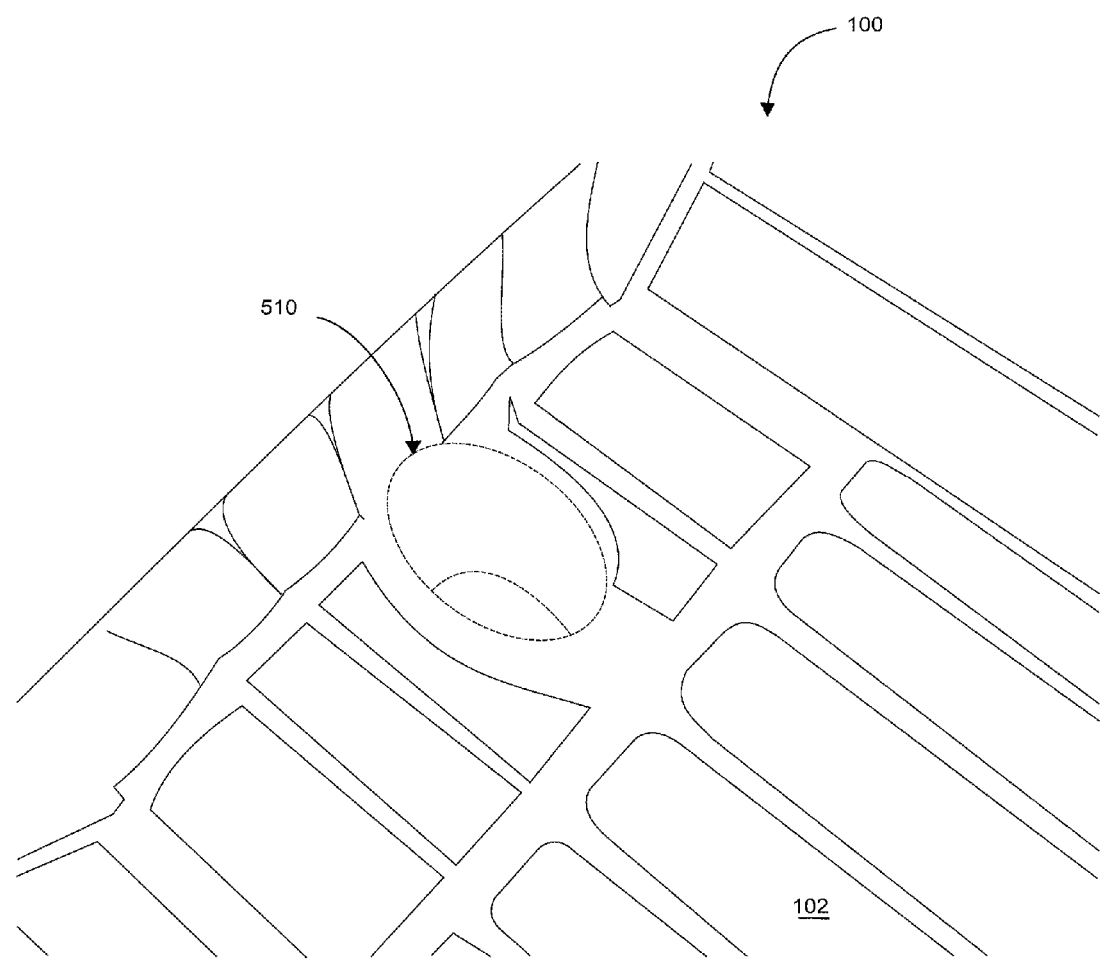
FIG. 5 is a perspective view illustrating a cup-holder of the Luminous Envy Tanning Float system according to an embodiment of the present invention of FIG. 1.

Referring now to FIGS. 4 & 5 showing perspective views of inflatable flotation device 102 of Luminous Envy Tanning Float system 100 according to an embodiment of the present invention. Pair of angled reflective, tan wings 110 preferably comprise polyethylene terephthalate (boPET) and preferably are angled at approximately a 45-degree angle relative to cushioned core-supported portion 120 to increase exposure to sunlight during at least one sunbathing period, thereby increasing tanning efficiency. Further, cushioned core-supported portion 120 preferably also comprises polyethylene terephthalate (boPET) to also increase exposure to sunlight during at least one sunbathing period. It should be appreciated that reflective material such as used on pair of angled reflective, tan wings 110 may comprise other suitable equivalents such that the sun's rays are suitably reflected for example other mirror-like surfaces, foils, paints, coatings, coverings and the like. Within the present invention PVC sheet having super transparent and/or super silver PVC sheets may be preferably used. The reflective material works like a mirror wherein the transparent sheet is used to collect the light and let light go through, then the silver sheet reflects the light collected. In this way when an individual lies on the present invention, the light can reach almost everywhere on the body thereby enabling an even tan. As mentioned, other suitable equivalents for enabling reflection means may be used with the present invention and will still be considered to be within the scope as described.

Inflatable flotation device 102 preferably comprises side air chambers that angle out 45 degrees from a main body of inflatable flotation device 102. These side air chambers allow user-sunbather to inflate via air inflatable flotation device 102 to a user-chosen firmness.

Inflatable flotation device 102 further comprises at least one cup holder 510 as shown best in FIG. 5. Cup holder 510 is preferably located on a far right side of inflatable flotation device 102 approximately 28-inches from a bottom position of pillow 130. Cup holder 510 provides a means for removably containing hydrating means such as cans or bottles of beverages. Further, cup holder 510 may be used to hold other items such as sun-tanning lotion and the like. Additionally, inflatable flotation device 102 preferably comprises at least one warning label 410. Warning label 410 may prevent user-sunbather 180 from obtaining at least one sunburn, mild or severe.

Luminous Envy Tanning Float system 100 according to an embodiment of the present invention of FIGS. 1-5 may comprise kit 540. Kit 540 may comprise the following parts: inflatable flotation device 102; pillow 130; a matching cup; and a set of user instructions. Upon reading this specification, it should be appreciated that, under appropriate circumstances, considering such issues as design preference, user preferences, marketing preferences, cost, structural requirements, available materials, technological advances, etc., other kit contents or arrangements such as, for example, including more or less components, customized parts, different color combinations, air pumps, parts may be sold separately.

Figure 6:
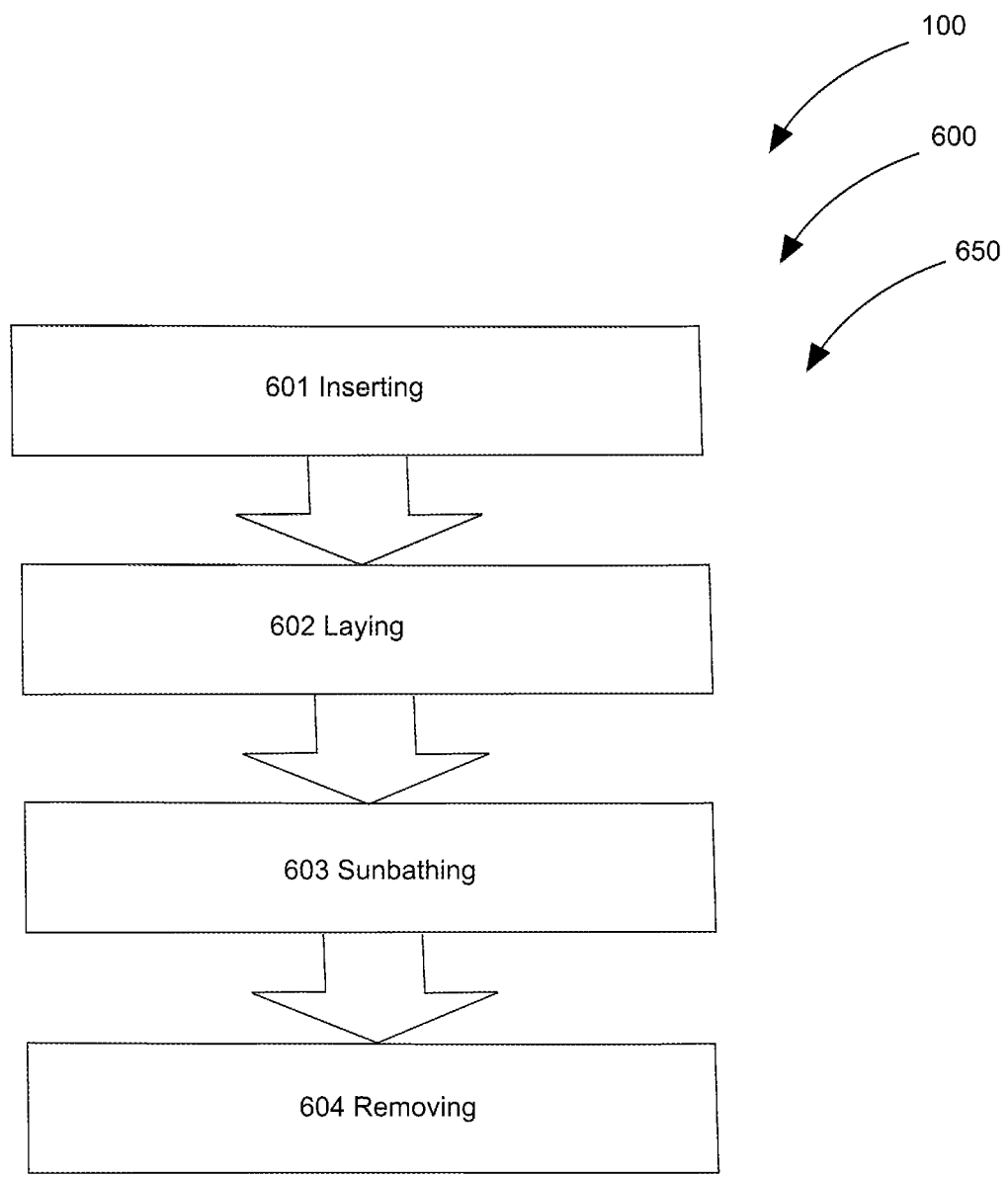
FIG. 6 is a flowchart illustrating a method of use according to an embodiment of the present invention of FIGS. 1-5.

Referring now to FIG. 6. showing a flowchart illustrating method of use 600 according to an embodiment of the present invention of FIGS. 1-5. A method (at least herein embodying method of use 600) of using inflatable flotation device 102 preferably comprising the steps of: step one 601 inserting inflatable flotation device 102 into a body of water; step two 602 laying on inflatable flotation device 102; step three 603 sun-bathing while supported by inflatable flotation device 102 and thereby promoting an even and accelerated tan; and step four 604 user 180 removing themselves from inflatable flotation device 102 when finished sun-bathing.

It should be noted that the steps described in the method of use can be carried out in many different orders according to user preference. Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. An inflatable flotation device to promote even and accelerated tanning adapted for use in water comprising:
   a pair of angled reflective, tan wings to direct the sunrays onto a user-sunbather from various angles comprising polyethylene terephthalate (boPET) to increase exposure to sunlight during said at least one sunbathing period;
   a cushioned core-supported portion comprises polyethylene terephthalate (boPET) to increase exposure to sunlight during the sunbathing period;
   a pillow;
   at least one cup holder; and
   at least one warning label;
   wherein said pair of pair of angled, reflective, tan wings are permanently attached to said cushioned core-supported portion providing supports for arms of said user-sunbather to be positioned for tanning;
   wherein said cushioned core-supported portion comprises a cushioning surface for a core-support of said user-sunbather;
   wherein said pillow is removeably-attachable to said cushioned core-supported portion and is inflatable to a user-preferred volume;
   wherein said user-sunbather is comfortably supported via said inflatable flotation device for even and accelerated tanning during at least one sunbathing period on a body of said water;
   wherein said cup holder is on a far right side of said inflatable flotation device approximately 28-inches from a bottom position of said pillow;
   wherein said at least one warning label prevents at least one sunburn;
   wherein said inflatable flotation device comprises clear plastic;
   wherein said inflatable flotation device measures approximately three-feet in width, six-feet wide, and eight-inches thick when in an in-use condition wherein said inflatable flotation device is inflated with air;
   wherein said three-foot width provides said user-sunbather room to find a position that exposes a body of said user-sunbather to said sun without tipping over into said water;
   wherein said inflatable flotation device reflects sunrays onto said user-sunbather;
   wherein said pillow provides a neck angling at a 45-degree angle to a final thickness of approximately eight-inches at the top of the head;
   wherein said pillow is contoured to fit a face of said user-sunbather when in a face-down position while lying on said inflatable flotation device;
   wherein said pair of angled, reflective, tan wings are angled at approximately a 45-degree angle relative to said cushioned core-supported portion; and
   wherein said inflatable flotation device comprises side air chambers that angle out 45 degrees from a main body of said inflatable flotation device, and wherein said inflatable flotation device may comprise a user-preferred color.

2. The inflatable flotation device to promote even and accelerated tanning adapted for use in water of claim 1 further comprising a kit including: said inflatable flotation device; at least one removably-coupleable pillow; a matching cup; and a set of user instructions.

* * * * *